United States Patent
Braun et al.

(10) Patent No.: US 6,423,866 B1
(45) Date of Patent: Jul. 23, 2002

(54) PRODUCTION OF AMINOHALOGENCROTONATES

(75) Inventors: Max Braun, Wedemark; Francine Jannssens, Vilvoorde; Werner Rudolph, Hannover; Kerstin Eichholz, Langenhagen, all of (DE)

(73) Assignee: SolvaytFlour und Derivate GmbH, Hannover (DE)

( * ) Notice: Subject to any disclaimer, the term of this patent is extended or adjusted under 35 U.S.C. 154(b) by 0 days.

(21) Appl. No.: 09/530,909

(22) PCT Filed: Oct. 29, 1998

(86) PCT No.: PCT/DE98/03263

§ 371 (c)(1),
(2), (4) Date: Jun. 6, 2000

(87) PCT Pub. No.: WO99/24390

PCT Pub. Date: May 20, 1999

(30) Foreign Application Priority Data

Nov. 7, 1997 (DE) .......................... 197 49 171
Nov. 7, 1997 (DE) .......................... 197 49 172

(51) Int. Cl.$^7$ .......................... C07C 229/00
(52) U.S. Cl. .......................... 560/172; 560/38
(58) Field of Search .......................... 560/38, 172

(56) References Cited

U.S. PATENT DOCUMENTS

| | | | |
|---|---|---|---|
| 5,304,665 A | * | 4/1994 | Cooper et al. |
| 5,399,543 A | | 3/1995 | Theodoridis ............... 504/243 |
| 5,777,154 A | * | 7/1998 | Chong et al. |
| 5,910,602 A | | 6/1999 | Chong et al. ............... 560/172 |

FOREIGN PATENT DOCUMENTS

| | | |
|---|---|---|
| EP | 0 808 826 | 11/1997 |
| JP | 6-321877 | 11/1994 |

OTHER PUBLICATIONS

Pashkevich et al., (1986). Reaction of fluoroalkyl–B–ketoesters with ammonia. Bull. Acad. Sci. USSR Div. Chem. Sci (English translation), vol. 35, pp 1438–1442.*

Derwent Acc. No. 1995–041245. Sato et al. 3–substituted–4, 4,4–trifluorocrotonic acid ester derivatives preparation comprised dehydration reaction of trifluoroacetoacetic acid esters and substituted amines.*

Goure, "The Synthesis and Chemistry of 2–Hydroxy–4, 6–bis(trifluoromethyl) pyridine–5–carboxylates", Monsanto Agricultural Group, Jan.–Feb. 1993, pp. 71–80.

Walborsky et al., "Addition Reactions to Ethyl γ, γ, γ–Trifluorocrotonate", Journal of American Chemical Society, 1953, pp. 3241–3243.

Luts et al., "Novel 6–(Trifluoromethyl)cytosines and 6–(Trifluoromethyl)uracils", Journal of Heterocyclic Chemistry, Jun. 1972, pp. 513–522.

Pashkevich et al., "Reaction to Fluoroalkyl–β–Ketoesters with Ammonia", Inst. of Chem., Urals Scientific Center, Academy of Sciences of the USSR, Feb. 5, 1985, pp. 1438–1442 (XP–002097881).

Glaser, Methoden der organischen Chemie Band XI/1, 1957, pp 170–175 (XP–002097790).

Joullie et al., "Aminolysis of Esters of Negatively Substituted Acetic Acids", Journal of Organic Chemistry, 1956, pp. 1358–1362.

* cited by examiner

Primary Examiner—Paul J. Killos
Assistant Examiner—Mahreen Chaudhry
(74) Attorney, Agent, or Firm—Crowell & Moring LLP

(57) ABSTRACT

Lower alkyl esters of 3-amino crotonates substituted by halogen in the C-4 position, e.g. ethyl 3-amino-4,4,4-trifluoro-crotonate, in which the amino group optionally may be substituted by one or two C1 to C3 alkyl groups or by one or two aryl groups, e.g. phenyl, are synthesized by thermolysis of ammonium salts of corresponding lower alkyl esters of acetoacetic acid substituted in the C-4 position by halogen, and removal of the resulting water of reaction. The water of reaction may be removed by an entraining agent, which preferably has a specific gravity heavier than that of the aqueous phase which forms in the reaction. This minimizes yield losses due to the ammonium salt becoming dissolved in the aqueous phase and results in especially high yields. Formation of the ammonium salt and thermolysis can be carried out simultaneously. Alternatively, it is possible to start from a molten ammonium salt of the halogencrotonate, e.g. the salt of the lower alkyl ester of 4,4,4-trifluoroacetoacetic acid, or to produce the salt in situ, and to pass an inert gas through the molten salt under thermolytic conditions and in the absence of a solvent. In this way the desired product can be produced in high yield and in high purity. This alternative can be implemented as a continuous process.

15 Claims, No Drawings

PRODUCTION OF AMINOHALOGENCROTONATES

BACKGROUND OF THE INVENTION

The invention relates to a method of synthesizing lower alkyl 3-amino-crotonates, which are substituted at the C-4 atom by halogen and at the amino group by 1 or 2 hydrogen atoms and/or 1 or 2 $C_1$ to $C_3$ alkyl groups or 1 or 2 aryl groups.

Lower alkyl 3-amino-crotonates, substituted by halogen at the C-4 atom, especially lower alkyl 3-amino-4,4,4-trifluorocrotonates are used as building blocks in chemical synthesis. They can be used, for example, for synthesizing herbicidal uracil derivatives, as disclosed in U.S. Pat. No. 5,399,543.

A method of synthesizing such compounds is given by W. F. Goure in *J. Heterocyclic Chem.* 30 (1993), pages 71 to 80 and especially on page 75. Anhydrous ammonia is passed for a period of 1.5 hours at a temperature of 75° to 80° C. through methyl 4,4,4-trifluoroacetoacetate. Subsequently, the reaction mixture is kept for a further 3 hours at a temperature of 100° C. and then cooled to ambient temperature, taken up in diethyl ether, dried, concentrated and subjected to a bulb tube distillation. The yield was 59% of the theoretical.

The thermolysis of the ammonium salt in the presence of acetic acid and ethanol is described in the Japanese patent application JP 6/321877. The European patent application EP-A-0 808 826 discloses the synthesis of trihalogen crotonates using ammonium salts as a source of amine. The ammonium salt of the ester is not formed. The formation of esters of aminocrotonic acids from NH3 and esters of acetoacetic acid or esters of trifluoroacetoacetic acid with and without solvents is disclosed in Houben-Weyl, Methods of Organic Chemistry, Volumn XI/I (1957), pages 170–175, and by Pashkevich et al. in Bull. Acad. Sci. USSR Div. Chem. Sci 35 (1986), pages 1438–1442.

It is an object of the present invention to provide a method for synthesizing crotonates, which are halogen-substituted at the C-4 atom and selected from the group comprising lower alkyl esters of 3-amino-4,4,4-trifluoro-crotonates and lower alkyl 3-amino-4,4-difluoro-4-chloro-crotonates and lower alkyl 3-amino-4,4-difluoro-crotonates, with which method these products are obtained in high yield with a high degree of purity. This objective is accomplished by the method of the present invention.

The inventive method of synthesizing crotonates, which are halogen-substituted at the C-4 atom and selected from the group consisting of lower alkyl 3-amino-4,4,4-trifluoro-crotonates, lower alkyl 3-amino-4,4-difluoro-4-chloro-crotonates and lower alkyl 3-amino-4,4-difluorocrotonates, the amino group optionally being substituted by 1 or 2 $C_1$ to $C_3$ alkyl groups or by aryl groups, and lower alkyl denotes methyl, ethyl, n-propyl, and i-propyl, envisions the simultaneous formation under thermolytic conditions without addition of an acid, of water and lower alkyl 3-aminocrotonates substituted by halogen at the C-4 atom, the water formed being removed from the reaction mixture, in that a thermolysis reaction is carried out starting from the ammonium salt of the corresponding lower alkyl acetoacetate substituted at the C-4 atom by halogen, and in the presence of an entraining agent for the water formed, or in that, in the absence of a solvent, inert gas is passed through the molten ammonium salt of the lower alkyl acetoacetate substituted at the C-4 atom by halogen and by these means, water formed is removed from the reaction mixture.

Accordingly, the method can be carried out according to several alternative procedures. The first alternative is explained in the following.

This alternative of the inventive method for synthesizing crotonates, which are halogenated at the C-4 atom and are selected from the group comprising lower alkyl 3-amino-4,4,4-trifluorocrotonates, lower alkyl 3-amino-4,4-difluoro-4-chlorocrotonates and lower alkyl 3-amino-4,4-difluorocrotonates, in which the amino group optionally may be substituted by 1 or 2 $C_1$ to $C_3$ alkyl groups or by aryl groups, is characterized in that the appropriate ammonium salt of the lower alkyl acetoacetate, substituted at the C-4 atom by halogen, is thermolyzed in the presence of an entraining agent for the water formed during the thermolysis.

Pursuant to this embodiment, lower alkyl esters of 3-amino-4,4-difluorocrotonate can be synthesized from the ammonium salt (the nitrogen may be substituted especially completely by hydrogen or by hydrogen and 1 or 2 $C_1$ to $C_3$ alkyl groups) of the 4,4-difluoroacetoacetate ester. Lower alkyl esters of 3-amino-4,4-difluoro-4-chlorocrotonate are synthesized correspondingly from the salt of the 4,4-difluoro-4-chloroacetoacetate. Lower alkyl esters of 3-amino-4,4,4-trifluorocrotonate are synthesized similarly.

The required esters are commercial products or can be synthesized by the reaction of ketene with trifluoroacetyl chloride, difluorochloroacetyl chloride or difluoroacetyl chloride, followed by an esterification, as described by W. F. Goure, *J. Heterocyclic Chem.* 30 (1993), pages 71 to 80 and especially page 72.

The inventive method can be carried out starting from the ammonium salt. For example, the ammonium salt can be synthesized in a first step. It is then thermolyzed in a second step. Pursuant to a different embodiment, the ammonium salt is synthesized in situ and simultaneously thermolyzed. This embodiment can also be carried out continuously.

Preferably, 4,4,4-trifluorocrotonates are synthesized. The invention will be described further with reference to this preferred embodiment.

The following apply generally for all the alternatives of the present invention. A catalyzing agent, such as an acid, is not required and is not added. The amine or ammonia used is added as base and not as a salt, for example, of carboxylic acids. The term "lower alkyl" denotes methyl, ethyl, n-propyl and i-propyl. "Aryl" preferably refers to phenyl.

Preferably, crotonates, which have two hydrogen atoms at the amino group, are synthesized. The synthesis of methyl 3-amino-4,4,4-trifluorocrotonate or ethyl 3-amino-4,4,4-trifluorocrotonate is especially preferred.

Entraining agents are used, which do not enter into undesired reactions with the starting materials or with the products. Aliphatic hydrocarbons, aromatic hydrocarbons or halogenated aliphatic hydrocarbons, for example, are suitable. For example, benzene or toluene can be used as entraining agent. Entraining agents which have a higher density than the water phase that forms and therefore represent the lower phase are especially preferred. Halogenated hydrocarbons, such as trichloroethylene or carbon tetrachloride, are particularly suitable. Entraining agents of higher density extract the ammonium salt, which is present in the lighter water phase in the water separator and, in this way, decrease the loss in yield, especially in the case of products that sublime.

The synthesis is carried out under conditions at which the water-entraining agent boils. For the sake of simplicity, the reaction is carried out at ambient pressure; if so desired, the reaction can, of course, also be carried out at an elevated or a reduced pressure.

Preferably, the temperature of the reaction mixture falls within the range of 80° to 120° C. Naturally, the temperature used also depends on the boiling point of the entraining agent.

When water is no longer collected in the water separator, the entraining agent is removed, for example, by distillation and the remaining crude crotonate is purified by vacuum distillation (for example, the vacuum of a water jet pump). Ethyl 3-amino-4,4,4-trifluorocrotonate distills at a temperature of 55° to 57° C.

Pursuant to a second alternative, which is described in the following, the water of reaction is carried away by an inert gas. For this embodiment of synthesizing lower alkyl 3-aminocrotonates, which are substituted at the C-4 atom by halogen and selected from the group consisting of lower alkyl 3-amino-4,4,4-trifluorocrotonates, lower alkyl 3-amino-4,4-difluorocrotonates and lower alkyl 3-amino-4,4-difluoro-4-chlorocrotonates, provisions are made to start in the absence of a solvent from a molten ammonium salt of the lower alkyl ester of acetoacetic acid, which is halogenated at the C-4 atom and, under thermolytic conditions, to bring about the simultaneous formation of water and of lower alkyl 3-aminocrotonates, halogenated at the C-4 atom and, by passing an inert gas through the molten salt, to carry away from the reaction mixture the water formed by thermolysis. The nitrogen atom may be substituted by one or two $C_1$ to $C_3$ alkyl groups or by aryl groups.

Lower alkyl esters of 3-amino-4,4-difluorocrotonate can be synthesized correspondingly from the ammonium salt of the 4,4-difluoroacetoacetate ester. Lower alkyl esters of the 3-amino-4,4-difluoro-4-chlorocrotonate are synthesized correspondingly from the salt of the 4,4-difluoro-4-chloroacetoacetate ester. The procedure for synthesizing lower alkyl esters of 3-amino-4,4,4-trifluorocrotonate is similar.

The required esters are commercial products or can be synthesized by the reaction of ketene with trifluoroacetyl chloride, difluorochloroacetyl chloride or difluoroacetyl chloride, followed by an esterification, as described by W. F. Goure, J. Heterocyclic Chem. 30 (1993), pages 71 to 80 and especially page 72.

The term "lower alkyl," denotes the methyl, ethyl, n-propyl and i-propyl group. Preferably, lower alkyl represents methyl or ethyl. "Aryl" preferably refers to phenyl.

Preferably, the thermolysis reaction is carried out at a temperature ranging from the melting point of the salt or of the reaction mixture up to a maximum of 110° C. and especially up to a maximum of 105° C. Higher temperatures, such as those up to 120° C. or higher can also be used. At these higher temperatures, however, decomposition products may be formed to a slight extent. Very good results are achieved if the temperature of the reaction mixture falls within the range of 80° C. to 95° C. As inert gas, gases can be used, which do not react in an undesirable manner with the starting material or with the products formed. Advantageously, nitrogen, argon, helium or carbon dioxide or their mixtures are used as inert gas.

Preferably, 4,4,4-trifluorocrotonates are synthesized. The invention will be explained further with reference to this preferred embodiment.

In this variant, the inventive method can also be carried out so that initially the ammonium salt of the lower alkyl ester of the 4,4,4-trifluoroacetoacetic acid is synthesized by passing essentially anhydrous ammonia into and/or over the lower alkyl ester of the 4,4,4-trifluoroacetoacetic acid. The thermolysis, with melting of the resulting salt, can then take place in a second step, without requiring any further purification operations. The conversion and yield are quantitative. Because of its purity, the crotonate formed can be used without further purification as a starting material for the synthesis of, for example, herbicides.

Pursuant to a different embodiment of the invention, the formation of the ammonium salt of the lower alkyl ester of the 4,4,4-trifluoroacetoacetic acid and its thermolysis can also be carried out simultaneously in this variation. Appropriately, the lower alkyl ester of the trifluoroacetoacetic acid is heated, and essentially anhydrous ammonia is passed into and/or over the ester, and an inert gas is passed through the reaction mixture. For example, a tubular reactor can be used, and ammonia can be introduced at the bottom of the reactor. The ester can be introduced, for example, in the upper region of the reactor. The method can also be carried out continuously.

The phrase "in the absence of a solvent" means that, other than the reactants, no solvent, such as ethers, esters, aromatic or halogenated hydrocarbons, are not added. Only the lower alkyl acetoacetate used, which is halogenated at the C-4 atom, can be present in excess. In this case, the ammonium salt which is formed may be present in the molten state and/or dissolved in the ester. The inventive method comprises this embodiment. The term "molten" also comprises the dissolved state of the ammonium salt in the ester educt. To complete the reaction, the thermolytic conditions can be maintained for some time after the introduction of the ammonia is ended (the time of ending the introduction of ammonia can be checked, for example, by NMR analysis). The time at which complete reaction has taken place can be ascertained by means of NMR analysis. If desired, the resulting, rather pure product can be purified further by distillation. Even if such a distillation is carried out, the yield is still remarkably high.

The products are obtained in pure form. They can be purified further by distillation. Extraction of the crude product by means of solvents, as described in the state of the art, is not necessary in working up the reaction mixture.

The inventive method enables lower alkyl 3-amino-4,4,4-trifluorocrotonates to be synthesized by a simple method in high yield and with a high purity. It is thereby surprising that the removal of water brings about advantages. The dehydrating thermolysis, namely, is not an equilibrium reaction. Otherwise, a reverse reaction would have to be observed during the aqueous working up. This is evidently not the case.

The following examples are intended to explain the invention further without limiting its scope.

EXAMPLES

Procedure for synthesizing 3-amino-4,4,4-trifluoroethylcrotonate from ethyl 4,4,4-trifluoroacetoacetate with ammonia using various water entraining agents (entraining agents)

Examples 1 and 2

Carried out with specific lower density water entraining agents

Examples 3 and 4

Carried out with specific higher density water entraining agents

Starting Formulation (Applies to Examples 1 to 4)

92.05 g (0.50 moles) of ethyl 4,4,4-trifluroacetoacetate
14.04 g (0.85 moles) of ammonia 125 ml of solvent Set-up and Procedure

Example 1

Benzene as Water Entraining Agent

The ethyl 4,4,4-trifluroacetoacetate was transferred to a 250 ml 3-neck flask having a temperature probe, water separator and magnetic stirrer, and benzene was added until the flask was 80% full. The attached water separator (capacity about 40 ml) for water entraining agents of lower density, in which the lower phase represents the water phase, was also filled completely with benzene in order to shorten the start-up time of the experiment.

The solution was then heated to the boiling point of benzene, until there was uniform refluxing. At this temperature, ammonia was introduced for 30 minutes, an exothermic reaction taking place. As the reaction progressed, the clear solution became cloudy (initially, the intermediate ammonium salt $NH_4^+[CF_3COCHCO_2Et]^-$ is formed). During the reaction, this ammonium salt tends to sublime (deposits form in the reflux condenser of the water separator). Reflux was continued for one hour after the introduction of ammonia was terminated. After cooling, the contents of the flask and the upper phase of the water separator consisted only of benzene and the desired product. Part of the ammonium salt was dissolved in the water phase. There conversion to the crotonate was 91%.

Example 2

Toluene as Water Entraining Agent

The procedure was the same as in Example 1, except that the reaction was carried out at 110° C. The conversion of the ethyl 4,4,4-trifluroacetoacetate to the crotonate was quantitative.

Example 3

Trichloroethylene as Entraining Agent

The procedure was the same as in Example 1, except that the reaction was carried out only at 93° C. and that a water separator for water-entraining agents of higher density was used; in this separator the water phase was removed as the upper phase. Ammonium salts, entrained by sublimation and dissolved in the water phase during the reaction were returned to the reaction flask once again here by the perpetual extraction by the water-entraining agent. After a total of 4 hours of boiling, a conversion of 99% of the ethyl 4,4,4-trifluoroacetate to the crotonate was attained.

Example 4

Carbon Tetrachloride as Entraining Agent

The procedure was the same as in Example 3, except that the reaction temperature was 85° C. The conversion was 86.35%.

Work-up of the Product (Applies to All the Experiments)

In all the Examples, pure crotonate was obtained by subsequently combining the flask contents with the entraining agent phases, distilling the water-entraining agents off in a rotary evaporator and distilling the residues under the vacuum of a water jet pump, the 3-amino-4,4,4-trifluoroethylcrotonate distilling over at 55° to 57° C. The isolated yields amounted to between 80% and 90% of the theoretical.

Examples 5 to 9

Synthesis with Introduction of Inert Gas

I) Experimental procedure for one-step synthesis of ethyl 3-amino-4,4,4-trifluorocrotonate from ethyl 4,4,4-trifluoroacetoacetate and ammonia Apparatus for Examples 5 to 7

The apparatus was composed of a 25 mm diameter glass tube, which is 200 mm long and provided with a double jacket for oil heating and to the top of which a 250 ml 3-neck flask is fused, on which a reflux condenser, the temperature of which is controlled at 50° C., is placed. The interior of the glass tube is filled completely with educt. About 50 mm below the fused-on 3-neck flask, there is a frit which extends into the interior of the glass tube and through which nitrogen is introduced during the experiment to blow out the water of reaction formed. The ammonia is supplied via a frit installed in the bottom of the glass tube.

Example 5

Starting Formulation 226.8 g (1.23 moles) of ethyl 4,4,4-trifluoroacetoacetate
22.1 g (1.30 moles) of ammonia Set-up and Procedure Ethyl 4,4,4-trifluoroacetoacetate (226.8 g, 1.23 moles) was added to the reaction tube, and the internal temperature was raised to about 100° C. and maintained there with the help of a thermostat. A nitrogen flow of about 100 liters/hour was now started, and 22.1 g (1.23 moles) of ammonia was introduced over a period totaling 48 minutes. After 5.0 g, 10.8 g, 15.4 g and 21.8 g of ammonia, respectively, a liquid sample was taken from the upper region of the apparatus for NMR analysis. A reaction sample, taken after 50% of the ammonia, corresponding to ammonia stoichiometry, had been added, clearly shows the formation of 3-amino-4,4,4-trifluoroethylcrotonate. The water-containing precursor of the crotonate, $NH_4^+[CF_3COCHCO_2Et]^-$, was present in the sample only to the extent of about 10%. When the introduction of ammonia was completed, the ammonium salt still constituted about 13%. For this reason, boiling was continued for a further 30 minutes. After this time, all the ammonium salt had been converted to the 3-amino-4,4,4-trifluoroethylcrotonate. Subsequently, a fractional distillation was carried out at 15 to 18 mbar. After a first fraction of educt, the pure product was obtained at 56 to 57° C. as a colorless liquid, which solidified at room temperature (melting point: 26° C.). The yield of isolated crotonate was 84% of the theoretical.

Example 6

The procedure was the same as in Example 5, except the reaction was carried out at 90° C. At a reaction temperature of 90° C., 38% of the ammonium salt was still present when the introduction of ammonia was ended and, after boiling for 30 minutes, 14% was still present. Finally, after boiling for 1.5 hours, the ammonium salt intermediate was converted completely to the crotonate.

Example 7

The procedure was the same as in Example 5, except that the reaction was carried out at 110° C. At a reaction temperature of 110° C., the ammonium salt had indeed been converted completely to the crotonate when the introduction of ammonia was concluded. However, besides ethanol, trifluoroacetone was detected in the nitrogen stream. This indicated incipient decomposition of the educt.

II) Experimental procedure for two-step synthesis of ethyl 3-amino-4,4,4-trifluorocrotonate from ethyl 4,4,4-trifluoroacetoacetate and ammonia via the ammonium salt of ethyl 4,4,4-trifluoroacetoacetate ($NH_4^+[CF_3COCHCO_2Et]^-$)

Example 8

Step 1: Synthesis of $NH_4^+[CF_3COCHCO_2Et]^-$:
Starting Formulation
ethyl 4,4,4-trifluoroacetoacetate (ETFAA) 210.0 g (1.14 moles) ammonia 15.3 g (0.90 moles)
Set-up and Procedure The ETFAA was added to a 250 ml multi-neck flask with KPG stirrer, temperature probe and dry ice condenser. While stirring vigorously, ammonia was introduced very slowly. The solution became cloudy immediately, and ammonium salt crystals became visible. The reaction was exothermic and therefore was cooled in a cold water bath. The rate of introduction was reduced so that a temperature of 40° C. was not exceeded. The suspension constantly became more pasty and solid and, for this reason, the stoichiometric amount of ammonia was not introduced.

The resulting crystals were filtered out with suction over a Blauband filter, and the residue remaining in the flask was transferred with 2×10 ml of a wash solution (hexane:ethyl acetate 9:1). The filter cake was stirred up once again and washed 3 times with 10 ml portions of the above wash solution in order to wash out the excess ETFAA used as a solvent. The ammonium salt consisted of white fine crystals, the consistency of which became powdery only after the washing. By this procedure, 170.3 g of 99% pure ammonium salt were obtained. This corresponds to an isolated yield of 94.09% of the theoretical. The crystals were analyzed and their purity determined by NMR.
NMR Data

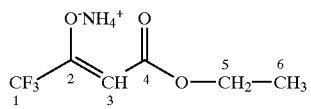

The NMR data of the substance shows the following chemical shifts:
$^{13}$C-NMR (100 MHz, DMSO): δ (ppm)=119.9 (C-1); 166.1 (C-2); 77.9 (C-3); 167.8 (C-4); 56.6 (C-5); 14.7 (C-6). Like the $^{13}$C data, the 400 MHz $^1$H data was in agreement with the nominal structure.

Example 9

Step 2: Thermolysis of $NH_4^+[CF_3COCHCO_2Et]^-$ to 3-amino-4,4,4-trifluoroethylcrotonate:

The ammonium salt (50 g) was filled into a 100 ml 3-neck flask with a nitrogen feed. The flask was provided with a reflux condenser and placed in an oil bath heated to 120° C. and the flow of nitrogen was started through the melt to drive off the water. After 7 minutes, the salt had melted completely (T=84° C. at sampling time). An initial sample for NMR analysis was taken from the melt. At this point the conversion to the crotonate was already 38%. Further samples were taken at 15 minute intervals to check the conversion. After 60 minutes the conversion was 98%, and after 90 minutes ammonium salt could no longer be detected. The yield of 3-amino-4,4,4-trifluoroethylcrotonate was quantitative.

Because of the selective reaction, the crotonate can be used for subsequent syntheses without further purification.

| Time (min) | Conversion (NMR) | Reaction Temperature |
|---|---|---|
| 0 | 38% | 84° C. |
| 15 | 77% | 95° C. |
| 30 | 90% | 94° C. |
| 60 | 98% | 95° C. |
| 90 | 100% | 95° C. |

The Table shows that a quantitative conversion was already reached after 90 minutes with the desired product being selectively formed.
NMR Data

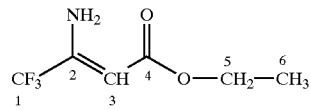

The NMR data of the substance shows the following chemical shifts:
$^{13}$C-NMR (100 MHz, DMSO): δ (ppm)=120.6 (C-1); 147.6 (C-2); 82.6 (C-3); 168.2 (C-4); 59.1 (C-5); 14.2 (C-6). Like the $^{13}$C data, the 400 MHz $^1$H data was in agreement with the nominal structure.

Example 10

One-step synthesis of trifluoroethylmethylaminocrotonate from ethyl 4,4,4-trifluoroacetoacetate and methylamine
Starting Formulation
1.0 mole of ethyl trifluoroacetoacetate (ETFAA) 184.01 g
1.0 mole of methylamine 31.05 g
Apparatus The apparatus comprised a 25 mm diameter glass tube, which is 200 mm long and was provided with a double jacket for oil heating and to the top of which a 250 ml 3-neck flask is fused, on which a reflux condenser, the temperature of which is controlled at 70° C, is placed. The interior of the glass tube is filled completely with educt. About 50 mm below the fused-on 3-neck flask, there is a frit which extends into the interior of the glass tube and through which nitrogen is introduced to blow out the water of reaction formed during the experiment. The ammonia is supplied via a frit installed in the bottom of the glass tube.
Set-up and Procedure ETFAA was added to the apparatus, which was also used for the synthesis of the unsubstituted crotonate, and heated to 115° C. A mixture of 10 parts of nitrogen and one part of methylamine was then introduced at a rate of 2 g/min through the lower glass frit. In addition to producing the entraining effect, this mixing of the amine with inert gas before introduction into the reactor enables the reaction to be conducted without problems. Without the admixture of nitrogen, the inlet site would become clogged immediately because of the formation of the corresponding ammonium salt, and byproducts could be formed because of local overheating. The addition of the methylamine was stopped briefly every 20 minutes in order to thermolyze the ammonium salt completely. During this time, the nitrogen acts only as an entraining gas for the water that is formed. The waste gas of the apparatus is passed through a condenser maintained at 70° C. and into a downstream cold trap.

Subliming ammonium salt was washed down once again by the entrained ETFAA and thus returned to the reaction. When the introduction of the gas mixture was terminated, the flow of nitrogen was continued for a further two hours at a rate of 30 liters/hour and a temperature of 115° C. After this time, any ammonium salt crystals, still present, had decomposed, and the NMR sample showed a conversion of 98%. Aside from water, traces of ethanol and TFK hydrate, formed by the decarboxylation of ETFAA together with moisture, were also detected in the cold trap downstream from the apparatus. After cooling, 20 g of the oily amber colored substance was subsequently subjected to distillation in a bulb tube. At a vacuum of 15 mbar, pure n-methyl-substituted crotonate distilled over at a temperature of 75° to 80° C. in the bulb tube furnace.

NMR Data

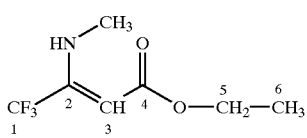

The NMR data of the substance shows the following chemical shifts:

$^{13}$C-NMR (100 MHz, CDCl$_3$): δ (ppm)=120.3 (C-1); 149.2 (C-2); 84.2 (C-3); 169.9 (C-4); 59.5 (C-5); 14.1 (C-6); 30.3 (C-7). Like the $^{13}$C data, the 400 MHz $^1$H data was in agreement with the nominal structure.

Example 11

One-step synthesis of trifluoroethyl phenylaminocrotonate from ethyl 4,4,4-trifluoroacetoacetate and aniline Starting Formulation 1.0 mole of ethyl trifluoroacetoacetate (ETFAA) 184.01 g
1.0 mole of aniline (freshly distilled) 93.1 g Set-up and Procedure The ETFAA is added to a 250 ml multi-neck flask with a reflux condenser maintained at 70° C. and a downstream cold trap and heated to 100° C. At this temperature, aniline is added dropwise, slowly and with constant stirring. At the same time, nitrogen is blown into the solution at a rate of about 50 liters/hour through a glass frit.

The reaction was slightly exothermic, and immediately after onset of the dropwise addition, the formation of the ammonium salt could be recognized. At the elevated temperatures, the crystals decomposed after a short time into water and crotonate. Due to the entraining effect of the nitrogen, the water formed was removed immediately from the equilibrium. However, the flow of nitrogen favored the sublimation of the ammonium salt, which was washed off once again from the cold trap by the likewise entrained ETFAA.

At the end of the dropwise addition, the solution was kept for a further hour at 100° C. in order to thermolyze the salt completely. The NMR sample at the end of the reaction shows 95% of the nominal component as well as residues of the educt. Aside from water, traces of TFK hydrate and ethanol were found once again in the cold trap.

NMR Data

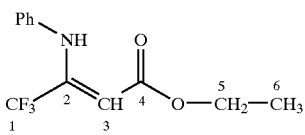

The NMR data of the substance shows the following chemical shifts:

$^{13}$C-NMR (100 MHz, CDCl$_3$): δ (ppm)=120.3 (C-1); 147.1 (C-2); 88.7 (C-3); 169.6 (C-4); 60.1 (C-5); 14.1 (C-6); 125.9; 126.5; 128.8; 138.4 (C-phenyl). Like the $^{13}$C data, the 400 MHz $^1$H data was in agreement with the nominal structure.

Example 12

Comparative Example

Thermolysis without inert gas, solvent or entraining agent

Thermolysis of NH$_4$$^+$[CF$_3$COCHCO$_2$Et]$^-$: to 3-amino-4,4,4-trifluoroethylcrotonate without inert gas:

Ammonium salt (50 g) was introduced into a 100 ml 3-neck flask. The flask was provided with a reflux condenser (cooling medium at 70° C.) and placed in an oil bath maintained at 120° C. After 90 minutes, ammonium salt could no longer be detected. At the surface of the suspension, "fat eyes", originating from water droplets, can be recognized. The NMR spectrum shows that by-products are present in addition to the 3-amino-4,4,4-trifluoroethylcrotonate. Even after a distillation, the theoretical product was obtained only with a purity of 97% because of contaminants and was isolated in a yield of 82%.

What is claimed is:

1. A method of synthesizing a lower alkyl crotonate substituted at the C-4 position by halogen and selected from the group consisting of lower alkyl 3-amino-4,4,4-trifluorocrotonates, lower alkyl 3-amino-4,4-difluoro-4-chlorocrotonates and lower alkyl 3-amino-4,4-difluorocrotonates, wherein the amino group is optionally substituted by one or two C$_1$ to C$_3$ alkyl groups or by one or two aryl groups, and the lower alkyl is selected from the group consisting of methyl, ethyl, n-propyl and isopropyl, said method comprising subjecting an ammonium salt of a lower alkyl acetoacetate substituted at the C-4 position by halogen to a thermolysis reaction in the presence of an entraining agent and without the addition of an acid, thereby simultaneously forming water and lower alkyl 3-aminocrotonates substituted by halogen at the C-4 atom, and removing entrained water during the thermolysis reaction, wherein an aqueous phase is produced by the water which is formed, and said entraining agent has a higher specific gravity than the aqueous phase, or said method comprising passing an inert gas through a molten ammonium salt of a lower alkyl acetoacetate substituted at the C-4 position by halogen in the absence of a solvent and without the addition of an acid, thereby simultaneously forming water and lower alkyl 3-aminocrotonates substituted by halogen at the C-4 atom and removing water from the reaction mixture.

2. A method according to claim 1, wherein the lower alkyl crotonate is a lower alkyl 3-amino-4,4,4-trifluorocrotonate substituted by hydrogen at the amino group.

3. A method according to claim 1, wherein the lower alkyl is methyl or ethyl.

4. A method according to claim 1, wherein said entraining agent is a halogenated hydrocarbon.

5. A method according to claim 1, wherein said entraining agent comprises trichloroethylene or carbon tetrachloride.

6. A method according to claim 1, wherein the ammonium salt is synthesized in situ, and the ammonium salt synthesis and the thermolysis are carried out simultaneously.

7. A method according to claim 1, wherein said method is carried out continuously.

8. A method of synthesizing a lower alkyl crotonate substituted at the C-4 position by halogen and selected from the group consisting of lower alkyl 3-amino-4,4,4-trifluorocrotonates, lower alkyl 3-amino-4,4-difluoro-4-chlorocrotonates and lower alkyl 3-amino-4,4-difluorocrotonates, wherein the amino group is optionally substituted by one or two $C_1$ to $C_3$ alkyl groups or by one or two aryl groups, and the lower alkyl is selected from the group consisting of methyl, ethyl, n-propyl and isopropyl, said method comprising passing an inert gas through a molten ammonium salt of a lower alkyl acetoacetate substituted at the C-4 position by halogen in the absence of a solvent and without the addition of an acid, thereby simultaneously forming water and lower alkyl 3-aminocrotonates substituted by halogen at the C-4 atom and removing water from the reaction mixture.

9. A method according to claim 8, wherein said method is carried out at a temperature in the range from the melting point of the salt or reaction mixture to at most 105° C.

10. A method according to claim 9, wherein said method is carried out at a temperature in the range from 80° C. to 95° C.

11. A method according to claim 8, wherein said inert gas is selected from the group consisting of nitrogen, argon, helium, carbon dioxide and mixtures of two or more of the foregoing.

12. A method according to claim 8, wherein said method comprises a first step in which the ammonium salt is synthesized by contacting the lower alkyl ester of the acetoacetic acid substituted at the C-4 atom by halogen with ammonia, and a second step in which the thermolysis is carried out.

13. A method according to claim 8, wherein the ammonium salt of the lower alkyl ester of the acetoacetic acid substituted at the C-4 position by halogen is synthesized in situ, and the ammonium salt synthesis and the thermolysis are carried out simultaneously to form the water and the lower alkyl 3-aminocrotonate substituted by halogen at the C-4 atom.

14. A method according to claim 8, wherein said method is carried out continuously.

15. A method according to claim 1, wherein an ammonium salt of a lower alkyl ester of 4,4,4-trifluoroacetoacetic acid is converted to a corresponding lower alkyl 3-amino-4,4,4-trifluorocrotonate.

* * * * *

UNITED STATES PATENT AND TRADEMARK OFFICE
CERTIFICATE OF CORRECTION

PATENT NO.    : 6,423,866 B1
DATED         : July 23, 2002
INVENTOR(S)   : Max Braun et al.

It is certified that error appears in the above-identified patent and that said Letters Patent is hereby corrected as shown below:

Title page,
Item [73], change the Assignee name from "SolvaytFlour und Derivate GmbH" to -- Solvay Fluor und Derivate GmbH --.

Signed and Sealed this

Twenty-fifth Day of February, 2003

JAMES E. ROGAN
*Director of the United States Patent and Trademark Office*